United States Patent [19]

Papenfuhs

[11] Patent Number: 5,869,710

[45] Date of Patent: Feb. 9, 1999

[54] POLYGDROXYALKYLAMIDOBETAINES

[75] Inventor: Bernd Papenfuhs, Neuötting, Germany

[73] Assignee: Hoechst Aktiengesellschaft, Frankfurt, Germany

[21] Appl. No.: 690,321

[22] Filed: Jul. 25, 1996

[30] Foreign Application Priority Data

Jul. 28, 1995 [DE] Germany .......................... 195 27 630.2

[51] Int. Cl.$^6$ .................................................. C07C 233/00
[52] U.S. Cl. ...................... 554/52; 252/351; 252/DIG. 7; 252/541; 252/544; 252/547
[58] Field of Search .............................. 284/52; 252/351, 252/541, 844, 547, DIG. 7

[56] References Cited

U.S. PATENT DOCUMENTS 5,464,565  11/1995  Hamann et al. ......................... 222/546

FOREIGN PATENT DOCUMENTS

| 4238211 | 1/1994 | Germany . |
| 4238207 | 5/1994 | Germany . |
| 4307475 | 9/1994 | Germany . |
| 95 14658 | 6/1995 | WIPO . |

Primary Examiner—Gary Geist
Assistant Examiner—Deborah D. Carr
Attorney, Agent, or Firm—Susan S. Jackson

[57] ABSTRACT

The betaine compounds described correspond to the following formula (1)

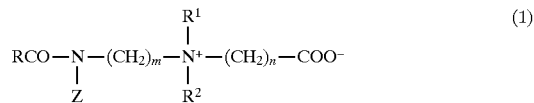

in which RCO is an aliphatic acyl radical having 6 to 22 carbon atoms, Z is a linear polyhydroxyhydrocarbon radical having at least 3 optionally oxyalkylated hydroxyl groups, m is an integer from 1 to 4, n is an integer from 1 to 4, $R^1$ is $C_1$ to $C_4$-alkyl or $C_2$ to $C_4$-hydroxyalkyl and $R^2$ is $C_1$ to $C_4$-alkyl or $C_2$ to $C_4$-hydroxyalkyl. The betaine compounds and the aqueous, alcoholic or aqueous-alcoholic solutions or dispersions thereof are prepared by betainization of a corresponding tertiary amine compound with a halogenocarboxylic acid or a halogenocarboxylic acid salt. The novel betaine compounds and their solutions are suitable, in particular, for the preparation of surface-active compositions for hair and body care.

7 Claims, No Drawings

POLYGDROXYALKYLAMIDOBETAINES

DESCRIPTION

The invention relates to polyhydroxyalkylamidobetaines, aqueous, alcoholic or aqueous-alcoholic solutions thereof, a process for the preparation of these betaines and their solutions, and the use of the novel betaine compounds and solutions thereof.

Betaines are valuable compounds from the group of zwitterionic surfactants. As a result of their good cleaning power and their other advantageous properties, in particular in respect of foam properties and skin tolerance, they are employed in the form of liquid formulations, above all for cleansing the hair and body. The solvents or dispersing agents are in general water, lower alkanols, such as methanol, ethanol and/or isopropanol, or a mixture thereof. Concentrated to highly concentrated (comprising as little solvent as possible) and at the same time low-viscosity formulations are desirable in respect of storage and transportation costs, further processing and on the spot use. The commercially available betaine solutions in general have a betaine content (active compound content) of less than 30% by weight. Concentrated betaine solutions are referred to in the case of an active compound content of 30 to about 35% by weight, and highly concentrated betaine solutions at an even higher active compound content.

Betaines are in general prepared by betainization of tertiary amine compounds with an ω-halogenocarboxylic acid or an ω-halogenocarboxylic acid salt in an aqueous or aqueous-alcoholic medium. Two variants are described in the prior art for achieving concentrated to highly concentrated betaine solutions or dispersions. In one variant, organic solubilizing agents are added to the reaction mixture, cf. U.S. Pat. No. 5,464,565. The other variant is based on seeking betaine compounds which have a good solubility in water or water/alcohol mixtures. Such betaines can advantageously also be employed directly for preparation of the concentrated to highly concentrated formulations mentioned. Such a route is described in DE-A-43 07 475. The compounds are betainized aminopolyols which have an improved water-solubility compared with other betaine compounds. DE-A-42 38 207 and DE-A-42 38 211, which describe water-soluble quaternized fatty acid polyhydroxyalkylamides, i.e. quaternary ammonium compounds, may also additionally be mentioned.

A novel class of betaines has now been found, which are distinguished by a good water-solubility and also give low-viscosity formulations with a high betaine concentration.

The betaine compounds according to the invention from the group of betainized polyhydroxyalkylamidoamines correspond to the following formula (1)

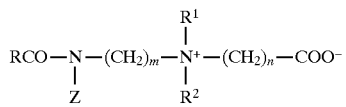

in which

RCO is an aliphatic acyl radical having 6 to 22 carbon atoms,

Z is a linear polyhydroxyhydrocarbon radical having at least 3 optionally oxyalkylated hydroxyl groups, m is an integer from 1 to 4, n is an integer from 1 to 4, $R^1$ is $C_1$ to $C_4$-alkyl or $C_2$ to $C_4$-hydroxyalkyl and $R^2$ is $C_1$ to $C_4$-alkyl or $C_2$ to $C_4$-hydroxyalkyl.

Preferred compounds of the formula (1) according to the invention are those in which RCO is a fatty acyl radical having 8 to 18 carbon atoms, Z is a radical of a sugar-alcohol which is derived from a reducing mono- or disaccharide, in particular from glucose, m is the number 3, n is the number 1 and $R^1$ and $R^2$ (identical or different) are methyl, ethyl or propyl.

The following may also be stated regarding RCO and Z: the aliphatic acyl radical RCO, which is preferably the fatty acyl radical mentioned, can be saturated or unsaturated (preferably mono- to triunsaturated). Examples which may be mentioned are the acyl radicals of caprylic, capric, lauric, palmitic, stearic and oleic acid, as well as coconut-acyl, tallow-acyl, preferably hydrogenated tallow-acyl, and the like. The fatty acid radical is often a mixture of two or more acyl groups, for example $C_{12}$ and $C_{14}$-acyl ($C_{12/14}$) $C_{16}$ and $C_{18}$-acyl ($C_{16/18}$) or $C_{12}$ to $C_{18}$-acyl. As already mentioned above, the linear polyhydroxyhydrocarbon radical preferably originates from sugar-alcohols derived from the group consisting of reducing sugars or reducing sugar derivatives. Preferred reducing sugars are the monosaccharides, preferably pentoses and hexoses, and the oligosaccharides, preferably disaccharides and, where appropriate, also trisaccharides. Examples of monosaccharides are glucose, galactose, mannose and talose as hexoses, and arabinose, ribose and xylose as pentoses. Of the monosaccharides, the hexoses are preferred. Examples of oligosaccharides (polysaccharides) are lactose, maltose, maltotriose and the like. Particularly preferred polyhydroxyalkyl radicals originate from reducing hexoses, in particular from glucose (sorbitly radical).

The betaine compounds of the formula (1) according to the invention are prepared by betainization of a tertiary amine compound of the formula (2)

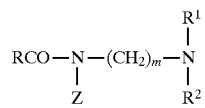

in which R, $R^1$, $R^2$, Z and m have the meanings given, with a halogenocarboxylic acid of the formula (3)

in which X is a halogen, preferably chlorine or bromine, and n has the meaning given, or with a salt thereof, preferably an alkali metal salt, in water, a lower alcohol or a mixture of water and a lower alcohol as the solvent (the betaine compound according to formula (1) being formed).

The reaction of the tertiary amine compound, for example N,N-dimethylaminopropyl-fatty alkyl-glucamide, and the halogenocarboxylic acid or halogenocarboxylic acid alkali metal salt is carried out, specifically, in a manner in which the tertiary amine and the betainizing agent are employed in a molar ratio of 1:1 to 1.2, preferably 1:1 to 1.05. The solvent can be water, a lower alcohol, preferably methanol, ethanol and/or isopropanol, or a mixture of water and the alcohols mentioned. The amount of solvent (which is introduced into the reaction mixture as such or in the form of solutions of the starting compounds) is in general chosen such that the betaine solution obtained after the reaction has a betaine content (active compound content) of 30 to about 65% by weight, and preferably 30 to 60% by weight, the percentages by weight being based on the solution or dispersion. The reaction temperature is in general 60° to 110° C., preferably 70° to 100° C. The betainization reaction, which proceeds under atmospheric pressure, is maintained until the desired conversion is achieved. The reaction mixture is kept at a pH of 7 to 12, preferably 7 to 10, from the start to the end of the reaction. An alkali metal hydroxide, which is added to the reaction mixture if it does not already have the pH mentioned, such as, for example, if the sodium salt of monochloroacetic acid is employed, is preferably used to adjust and maintain the pH mentioned. According to a preferred procedure, the tertiary amine and the solvent are initially introduced into the reaction vessel. The mixture is heated to 70° to 100° C. 1 to 1.2 mol, preferably 1 to 1.05 mol, of halogenocarboxylic acid, per mole of amine compound, in the form of a 60 to 80% strength by weight aqueous solution and an alkali metal hydroxide in the form of a 30 to 50% strength by weight aqueous solution, to adjust the pH of the solution or reaction mixture from 7 to 12, preferably 7 to 10, are introduced into the heated amine solution, while maintaining the temperature mentioned. The halogenocarboxylic acid solution and the alkali metal hydroxide solution are added alternately and in portions (in each case in about 3 to 4 portions), starting with the halogenocarboxylic acid. After each portion of halogenocarboxylic acid solution and alkali metal hydroxide solution has been introduced into the reaction mixture, the mixture is allowed to after-react until the halogenocarboxylic acid has reacted or until a uniform pH has been established. After the end of these additions, the reaction mixture is kept further at 70° to 100° C. under atmospheric pressure until the required betaine solution is present. In addition to the solvent and a little alkali metal salt, the resulting betaine solutions comprise the betaine compound according to the invention in a high concentration. It can be isolated by removing the solvent and the salt. This is in general unnecessary, because the betaines according to the invention are already employed above all in solutions.

The solutions according to the invention of betainized polyhydroxyalkylamidoamines essentially comprise A) 30 to 65% by weight, preferably 30 to 60% by weight, of at least one betaine compound of the formula (1) and B) water, a lower alcohol or a mixture of water and a lower alcohol as the remainder to make up to 100% by weight, the percentages by weight being based on the solution. The solutions according to the invention are prepared as described above.

The amine compounds of the formula (2) given which are required for preparation of the betaines according to the invention and their solutions are advantageously obtained by a) reaction of a polyhydroxyhydrocarbon compound from which the radical Z in formula (1) or formula (2) is derived with an amine of the formula (4)

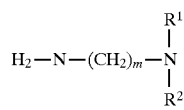
(4)

in which m, $R^1$ and $R^2$ have the meanings given, in an aqueous or aqueous-alcoholic medium and in the presence of a hydrogenation catalyst to give the polyhydroxyalkylamine of the formula (5)

(5)

in which Z, m, $R^1$ and $R^2$ have the meanings given, and b) reaction of the product obtained in step a), essentially comprising the polyhydroxyalkylamine of the formula (5), with a fatty acid alkyl ester of the formula (6)

(6)

in which R has the meaning given and $R^3$ is a $C_1$ to $C_3$-alkyl group, to give the polyhydroxyalkylamidoamine of the formula (2) given. Steps a) and b) are described in more detail below:

Step a) is a reductive amination of a polyhydroxylated compound of the abovementioned type, such as mono- or disaccharide compounds, preferably hexoses, such as glucose, with an amine of the formula (4). The sugar compound and the amine compound are employed in a molar ratio of about 1:1 to 1.2. The solvent, which is preferably water or a mixture of water and a lower alcohol, such as methanol, ethanol and/or isopropanol, is employed in an amount of about 30 to 50% by weight, based on the polyhydroxyalkylamine formed. Catalysts which can be employed are the customary hydrogenation catalysts, such as palladium-on-active charcoal, copper chromite and, in particular, Raney nickel in an amount of in general 0.01 to 3% by weight, preferably 0.1 to 1% by weight, based on the sugar compound to be aminated. The reductive amination reaction is carried out at a temperature of 40° to 150° C., preferably 50° to 120° C., and under a hydrogen pressure of 10 to 200 bar, preferably 20 to 100 bar. The amino-sugar compound according to formula (5) is obtained in practically quantitative yields.

In step b), the reaction product obtained in step a) (if appropriate after the catalyst has been filtered off) is acylated with about 1 mol of a fatty acid ester of the formula (6) per mole of amino-sugar compound, in the presence of a basic catalyst, preferably an alkali metal methlyate. This is preferably carried out at a temperature of about 60° to 130° C., for example by boiling the reaction mixture under reflux, and leads to the aclyated amino-sugar of the formula (2).

The betaine compounds according to the invention have unexpectedly good properties. They are soluble in water, lower alcohols or mixtures thereof at room temperature (20° to 25° C.) up to high concentrations. The concentrated to highly concentrated solutions are of surprisingly low viscosity at room temperature, i.e. are readily flowable, pourable, pumpable and the like. The low viscosity also exists if the betaine solutions comprise salts, such as sodium chloride or sodium bromide. The aqueous, alcoholic or aqueous-alcoholic betaine solutions according to the invention are, furthermore, distinguished by a high clarity (they look water-clear to the human eye) and storage stability. The betaines according to the invention are based on regenerating raw materials and are biologically degradable, which is a further advantage of these surfactant compounds with outstanding surfactant properties. On the basis of this profile of properties, the betaines and betaine solutions according to the invention are advantageously used for the preparation of surface-active compositions for hair and body care.

The invention will now be illustrated in more detail by examples.

EXAMPLE 1

113.6 g (0.25 mol) of N, N-dimethylaminopropyl-$C_{12/14}$-glucamide and 233.1 g of distilled water are initially introduced into a five-necked flask fitted with a reflux condenser, stirrer, thermometer and two dropping funnels, and the mixture is heated to 80° to 85° C., while stirring. 10.2 g (87 mmol) of an 80% strength aqueous monochloroacetic acid solution are then added at this temperature in the course of 15 minutes, the mixture is stirred for 30 minutes, 7.3 g (91 mmol) of a 50% strength aqueous NaOH solution are then added in the course of 10 minutes and the mixture is subsequently stirred for 5 minutes.

This procedure is repeated twice more, after which an after-reaction of 180 minutes follows. For an even more complete reaction, the reaction temperature is increased to 90° to 95° C., a further 1.1 g (14 mmol) of the NaOH solution are added to maintain a pH of 8 to 9 and stirring is continued for 8 hours. The resulting clear solution essentially comprises 32% by weight of a betaine of the formula (1), in which RCO is a $C_{12/14}$-fatty acyl radical, m is 3, n is 1, Z is a sorbityl radical and $R^1$ and $R^2$ are $CH_3$, NaCl and water to make up to 100% by weight. The solution is of low viscosity and is therefore readily pourable.

EXAMPLE 2

Batch size:
113.6 g (0.250 mol) of N,N-dimethylaminopropyl-$C_{12/14}$-glucamide
117.5 g of distilled water
30.6 g (0.263 mol) of 80% strength aqueous monochloroacetic acid solution
23.0 g (0.285 mol) of 50% strength aqueous NaOH solution
The reaction is carried out analogously to Example 1. The resulting clear solution essentially comprises 45% by weight of a betaine of the formula (1), in which RCO is a $C_{12/14}$-fatty acyl radical, m is 3, n is 1, Z is a sorbityl radical and $R^1$ and $R^2$ are $CH_3$, NaCl and water to make up to 100% by weight. In spite of its high betaine content, the solution is highly liquid (readily pourable) at room temperature and storage-stable, and shows no clouding or precipitation even after a relatively long storage time.

I claim:

1. A polyhydroxyalkylamidobetaine of the following formula (1)

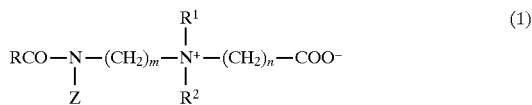

(1)

in which

RCO is an aliphatic acyl radical having 6 to 22 carbon atoms,

Z is a linear polyhydroxyhydrocarbon radical having at least 3 optionally oxyalkylated hydroxly groups, m is an integer from 1 to 4, n is an integer from 1 to 4, $R^1$ is $C_1$ to $C_4$-alkyl or $C_2$ to $C_4$-hydroxyalkly and $R^2$ is $C_1$ to $C_4$-alkyl or $C_2$ to $C_4$-hydroxyalkly.

2. A betaine as claimed in claim 1, in which, in formula (1),

RCO is a fatty acyl radical having 8 to 18 carbon atoms,

Z is a radical of a sugar-alcohol which is derived from a reducing mono- or disaccharide, m is the number 3, n is the number 1 and $R^1$ and $R^2$ (identical or different) are methyl, ethyl or propyl.

3. A betaine as claimed in claim 1, in which, in formula (1),

RCO is a fatty acyl radical having 8 to 18 carbon atoms,

Z is a sorbityl radical, m is the number 3, n is the number 1 and $R^1$ and $R^2$ (identical or different) are methyl, ethyl or propyl.

4. An aqueous, alcoholic or aqueous-alcoholic solution of a polyhydroxyalkylamidobetaine as claimed in claim 1, consisting essentially of A) 30 to 65% by weight of at least one compound of the formula (1) in claim 1 and B) water, a lower alcohol or a mixture of water and a lower alcohol as the remainder to make up to 100% by weight, the percentages by weight being based on the solution.

5. A solution as claimed in claim 4, in which component A) is present in an amount of 30 to 60% by weight.

6. A composition for hair and body care which comprises the compound of formula (1) as claimed in claim 1.

7. A composition for hair and body care which comprises the solution as claimed in claim 4.

* * * * *